(12) United States Patent  (10) Patent No.: US 7,798,144 B2
Kwok et al.                  (45) Date of Patent:    Sep. 21, 2010

(54) LIFE STYLE FLOW GENERATOR AND MASK SYSTEM

(75) Inventors: Philip Rodney Kwok, Chatswood (AU); Ron Richard, Temecula, CA (US); Muditha Pradeep Dantanarayana, Cherrybrook (AU); Larry Puckeridge, Marrickville (AU); Mark Bertinetti, Ermington (AU)

(73) Assignee: ResMed Limited, Bella Vista (AU)

( * ) Notice: Subject to any disclaimer, the term of this patent is extended or adjusted under 35 U.S.C. 154(b) by 1082 days.

(21) Appl. No.: 11/491,016

(22) Filed: Jul. 24, 2006

(65) Prior Publication Data

US 2007/0023044 A1      Feb. 1, 2007

Related U.S. Application Data

(60) Provisional application No. 60/703,432, filed on Jul. 29, 2005.

(51) Int. Cl.
    *A61M 11/00*     (2006.01)
(52) U.S. Cl. .................... 128/204.18; 128/897
(58) Field of Classification Search ............ 128/204.18, 128/200.21, 200.14, 203.12, 897
    See application file for complete search history.

(56) References Cited

U.S. PATENT DOCUMENTS 4,228,806 A     10/1980  Lidow
5,771,886 A      6/1998  Maire et al.
6,307,674 B1 *  10/2001  Sauer et al. ................. 359/443
6,543,449 B1 *   4/2003  Woodring et al. ...... 128/204.18
6,705,315 B2     3/2004  Sullivan et al.
7,350,520 B1 *   4/2008  Richard-Bey .......... 128/200.21
2001/0023698 A1* 9/2001  Addington et al. .......... 128/897
2003/0066529 A1  4/2003  Truschel et al.

FOREIGN PATENT DOCUMENTS

| WO | WO 02/02169   | 1/2002  |
| WO | WO 02/18002   | 3/2002  |
| WO | WO 03/024335  | 3/2003  |
| WO | WO 2005/028009| 3/2005  |
| WO | WO 2005/099798| 10/2005 |

OTHER PUBLICATIONS

Projection Alarm Clock, http://scientificsonline.com/product.asp?pn+3081174&bhcd2+1138900554 (pp. 2) (no. date).
SleepSmart, http://www.axonlabs.com/pr_sleepsmart.html, (no date).
Bio Alarm Clock, http://www.halfbakery.com/idea/bio_20alarm_20clock, pp. 3 , (no date).
U.S. Appl. No. 60/505,718, dated Sep. 2003, Kwok.

* cited by examiner

*Primary Examiner*—Steven O Douglas
(74) *Attorney, Agent, or Firm*—Nixon & Vanderhye P.C.

(57) ABSTRACT

A flow generator for generating a supply of pressurized air to be provided to a patient for treatment includes a housing, a blower provided to the housing, and a projection unit provided to the housing. The blower is operable to provide a pressurized flow of air at an outlet. The projection unit is operable to project an image onto a surface adjacent the housing.

19 Claims, 8 Drawing Sheets

LIFE STYLE FLOW GENERATOR AND MASK SYSTEM

CROSS-REFERENCE TO APPLICATIONS

This application claims the benefit of U.S. Provisional Application No. 60/703,432, filed Jul. 29, 2005, which is incorporated herein by reference in its entirety.

FIELD OF THE INVENTION

The present invention relates to flow generators and mask systems used in the treatment, e.g., of Sleep Disordered Breathing (SDB) with Non-Invasive Positive Pressure Ventilation (NIPPV).

BACKGROUND OF THE INVENTION

Known flow generators and mask systems are structured solely for generating and delivering a supply of pressurized air to be provided to a patient for treatment. The present invention provides improvements to known flow generators and mask systems to overcome this limitation in order to enhance and/or facilitate the treatment session.

SUMMARY OF THE INVENTION

One aspect of the invention is directed towards a flow generator including structure to facilitate or enhance sleeping by stimulating human senses such as sight, hearing, touch, and/or smell.

Another aspect of the invention is directed towards a flow generator and/or mask system that includes visual, audio, and/or aromatic medium to facilitate or enhance sleeping.

Another aspect of the invention relates to a flow generator for generating a supply of pressurized air to be provided to a patient for treatment. The flow generator includes a housing, a blower provided to the housing operable to provide a pressurized flow of air at an outlet, and an integral or detachable unit configured to stimulate human senses to assist in treatment and/or sleep cycle.

Another aspect of the invention relates to a flow generator for generating a supply of pressurized air to be provided to a patient for treatment. The flow generator includes a housing, a blower provided to the housing, and a projection unit provided to the housing. The blower is operable to provide a pressurized flow of air at an outlet. The projection unit is operable to project an image onto a surface adjacent the housing. In an embodiment, the projection unit may be controlled based on at least one monitored parameter of the patient.

Yet another aspect of the invention relates to a flow generator for generating a supply of pressurized air to be provided to a patient for treatment. The flow generator includes a housing, a blower provided to the housing, and an audio unit provided to the housing. The blower is operable to provide a pressurized flow of air at an outlet. The audio unit is operable to selectively generate at least one sound. In an embodiment, the audio unit may be controlled based on at least one monitored parameter of the patient.

Still another aspect of the invention relates to a flow generator for generating a supply of pressurized air to be provided to a patient for treatment. The flow generator includes a housing, a blower provided to the housing, and an aromatic unit provided to the housing. The blower is operable to provide a pressurized flow of air at an outlet. The aromatic unit is operable to selectively release at least one therapeutic aroma. In an embodiment, the aromatic unit may be controlled based on at least one monitored parameter of the patient.

Still another aspect of the invention relates to a mask assembly for delivering breathable gas to a patient. The mask assembly includes a patient interface structured to engage the patient's face and provide a seal, a headgear arrangement to support the patient interface in a desired position on the patient's face, and an audio and/or aromatic unit provided to at least one of the patient interface and the headgear arrangement. The audio unit operable to selectively generate at least one sound.

Still another aspect of the invention relates to a device for delivering drug or hormonal treatment. The device includes a sleep stage monitor structured to monitor a patient's sleep stage and a unit structured to release drug or hormonal treatment to a patient. The unit is communicated with the sleep stage monitor such that the release of drug or hormonal treatment is based on the patient's sleep stage.

Still another aspect of the invention relates to a substance delivery apparatus including a sensor to generate a sleep stage signal indicating a patient's sleep stage, and a delivery unit structured to release and/or deliver a therapeutic or medicinal substance via the patient's airways in accordance with the sleep stage signal.

Yet another aspect of the invention relates to a method for delivering a therapeutic or medicinal substance. The method includes sensing a patient to generate a sleep stage signal indicating a patient's sleep stage, and releasing and/or delivering a therapeutic or medicinal substance via the patient's airways in accordance with the sleep stage signal.

Yet another aspect of the invention relates to a flow generator for generating a supply of pressurized air to be provided to a patient for treatment. The flow generator includes a control unit to operate the flow generator and an alarm to wake the patient from sleep.

Other aspects, features, and advantages of this invention will become apparent from the following detailed description when taken in conjunction with the accompanying drawings, which are a part of this disclosure and which illustrate, by way of example, principles of the invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
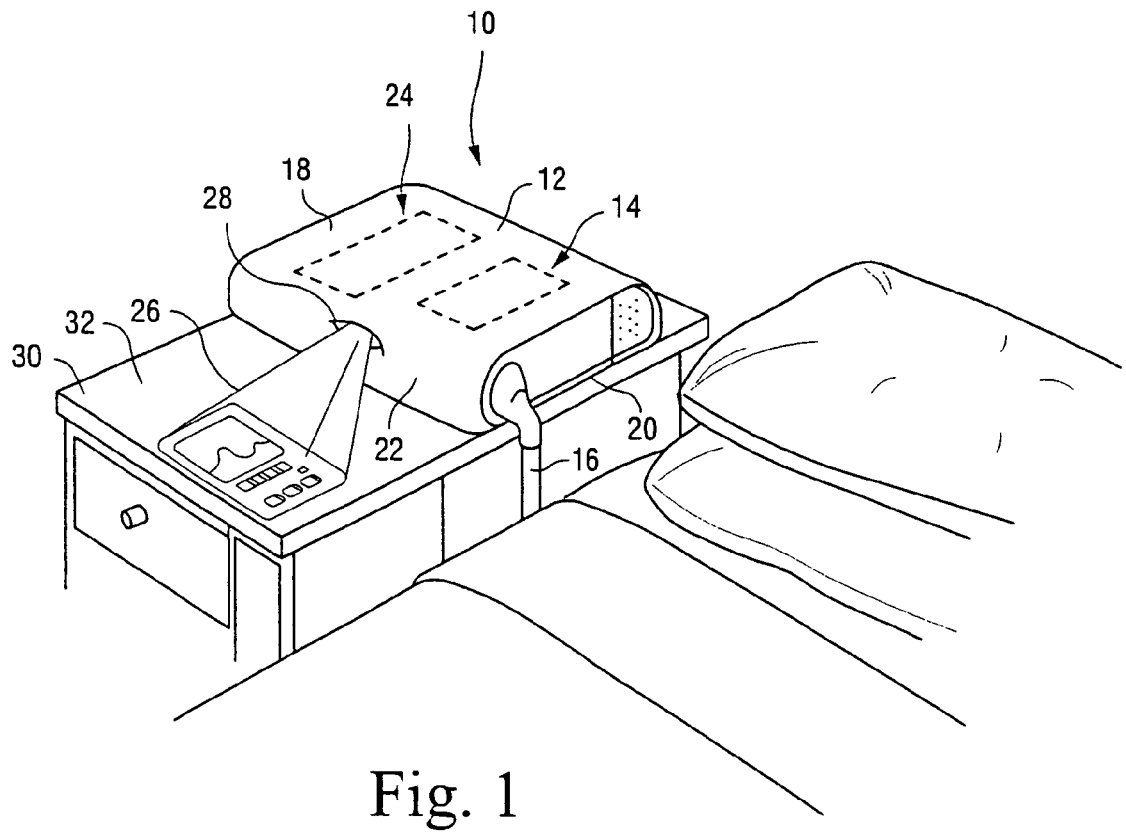
FIG. 1 is a perspective view of a flow generator constructed according to an embodiment of the present invention, the flow generator including a projection unit operable to project an image onto a surface.
Figure 2:
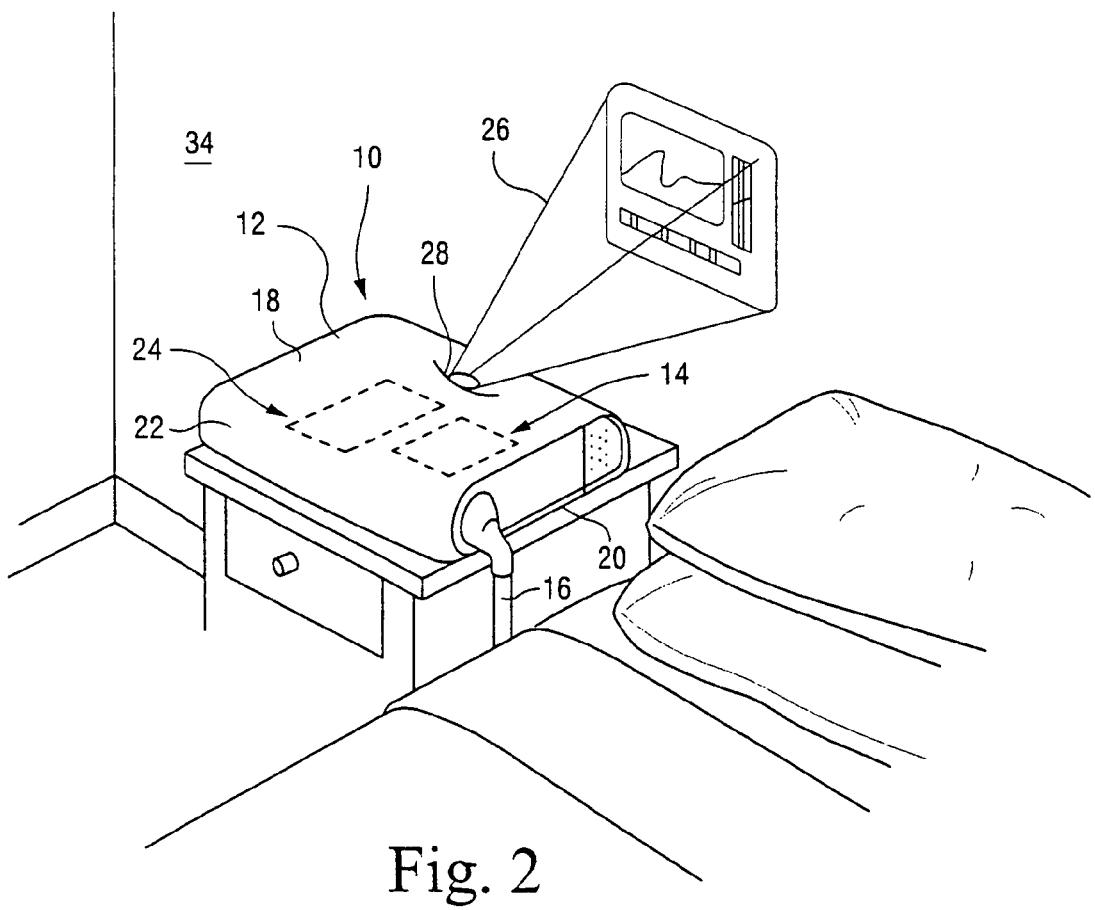
FIG. 2 is a perspective view of a flow generator constructed according to another embodiment of the present invention, the flow generator including a projection unit operable to project an image onto a surface.
Figure 3:
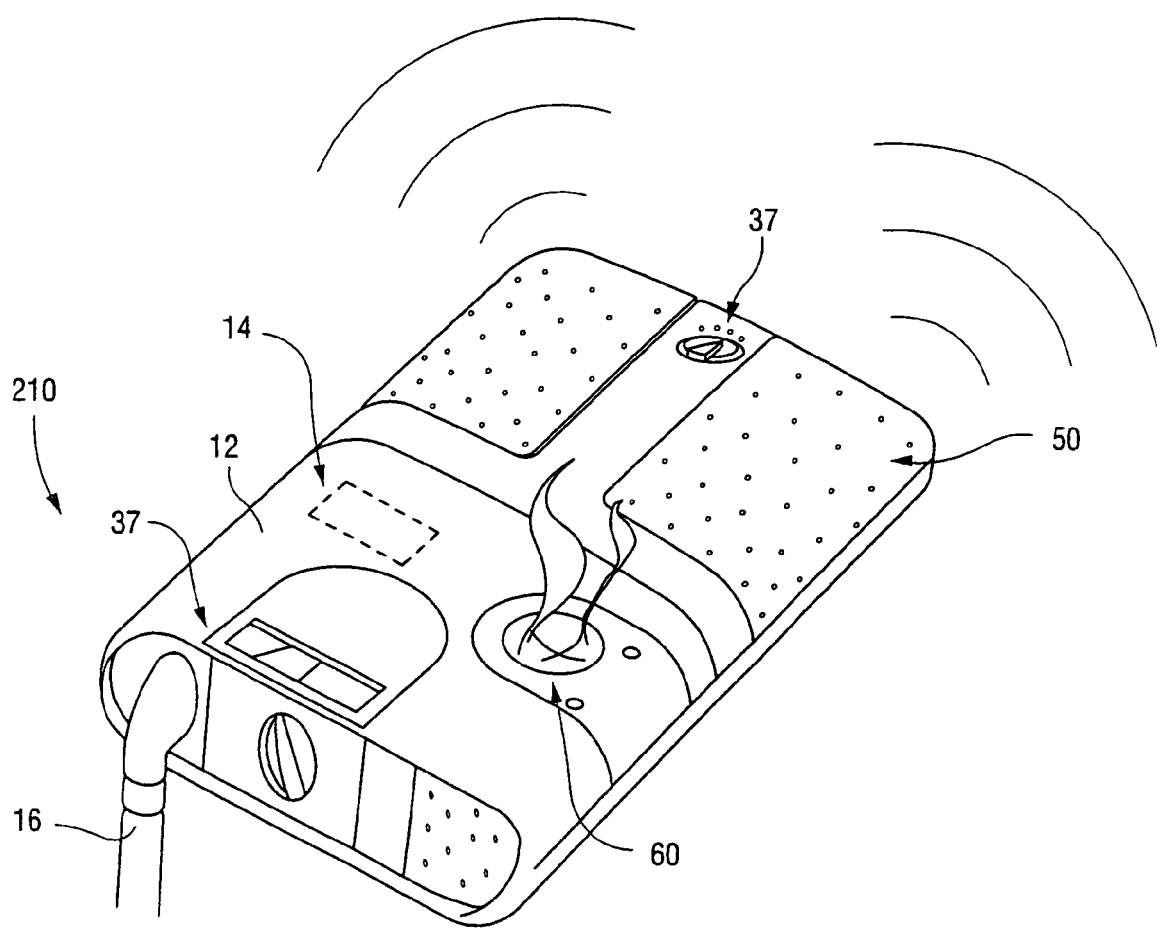
FIG. 3 is a perspective view of a flow generator constructed according to another embodiment of the present invention, the flow generator including an audio unit operable to selectively generate at least one sound and an aromatic unit operable to selectively release at least one therapeutic aroma.

FIGS. 1-3 illustrate flow generators 10, 210 constructed according to embodiments of the present invention. The flow generators 10, 210 are structured to generate a supply of pressurized air to be provided to a patient for treatment, e.g., of Sleep Disordered Breathing (SDB) and Non-Invasive Positive Pressure Ventilation (NIPPV). Moreover, the flow generators 10, 210 include visual, audio, and/or aromatic medium to enhance and/or facilitate the treatment session by stimulation of human senses as discussed in greater detail below.

Flow Generator with Projection Unit

As shown in FIG. 1, the flow generator 10 includes a housing 12 and a blower 14 supported within the housing 12. As is known in the art, the blower 14 is operable to draw a supply of air into the housing 12 through one or more intake openings and provide a pressurized flow of air at an outlet. The supply of pressurized air is delivered to the patient via an air delivery conduit 16 that includes one end coupled to the outlet of the flow generator 10 and an opposite end coupled to a patient interface 38 (e.g., see FIGS. 5-7). The patient interface 38 comfortably engages the patient's face and provides a seal. The patient interface 38 may have any suitable configuration as is known in the art, e.g., full-face mask, nasal mask, oro-nasal mask, mouth mask, nasal prongs, etc. Also, any suitable headgear arrangement 40 (e.g., see FIGS. 5-7) may be utilized to comfortably support the patient interface 38 in a desired position on the patient's face.

As illustrated, the housing 12 of the flow generator 10 includes an upper wall 18, a lower wall 20, and side walls 22 that interconnect the upper and lower walls 18, 20. A projection unit 24 is supported by or within the housing 12. The projection unit 24 is operable to project an image 26 through one of the walls 18, 20, 22 and onto a surface adjacent the housing 12. Specifically, the projection unit 24 includes a light source that casts the image 26 through a lens provided adjacent an opening 28 in one of the walls 18, 20, 22.

As shown in FIG. 1, the housing 12 may be supported on a bedside table 30. The opening 28 is provided in one of the side walls 22 of the housing 12 such that the image 26 is projected onto an upper surface 32 of the bedside table 30.

However, the opening 28 may be provided in any one of the walls 18, 20, 22 to allow the image 26 to be projected onto any suitable surface. For example, FIG. 2 illustrates a flow generator 10 wherein the opening 28 is provided in the upper wall 18 of the housing 12 such that the image 26 is projected onto a surface 34 of an adjacent wall. However, the projection unit 24 may be adjustable to allow the patient to select the desired surface to project the image 26.

The image 26 projected by the projection unit 24 shown in FIGS. 1 and 2 may take various forms, and may be configured to enhance and/or facilitate the treatment session. For example, the image 26 may be configured to facilitate and/or sustain sleeping. The image 26 may include a recording, e.g., including audio/visual instructions on how to operate the flow generator, fit the mask, adjust headgear, etc. The image 26 may take the form of a live feed, e.g., where a patient seeks live assistance from a clinician, or where the clinician is remotely monitoring a parameter of the patient and wants to convey a corrective action or other instructions to the patient.

As shown in FIGS. 1 and 2, the image 26 may include a control panel that illustrates one or more parameters of the flow generator 10, e.g., treatment pressure, and/or the patient, e.g., heart-rate. Also, the projected control panel may include known virtual keyboard technology that enables the patient to adjust the one or more parameters via the projected control panel. For example, the projected control panel may include projected keyboard and/or arrow keys that can be selected by the patient or clinician to adjust the magnitude of the treatment pressure.

In another embodiment, the image 26 may include a visual show that includes variably changing colors and/or images. For example, the projection unit 24 may illuminate the adjacent surface in relaxing images selected to facilitate sleep.

In yet another embodiment, the projection unit 24 may be configured to project a clock, television programs, movies, and/or internet sites. The projection unit 24 may be digital or any other suitable technology.

Flow Generator with Audio and/or Aromatic Unit

FIG. 3 illustrates an embodiment of a flow generator 210 that includes an audio unit 50 and/or an aromatic unit 60 supported by or within the housing 12. Thus, the flow generator 210 forms a relaxation system that utilizes audio and/or aromatic medium to facilitate and/or sustain sleeping. It should be understood that the projection unit 24, audio unit 50, and aromatic unit 60 may be provided separately in the flow generator 10, 210, or in any combination.

The audio unit 50 is operable to selectively generate, e.g., via a speaker, at least one sound that passes through one or more openings, e.g., mesh, provided in selected walls of the housing 12. In an embodiment, the sound may be in the form of music, soothing sounds, white noise, and/or noise canceling. The soothing sounds may be, e.g., sounds of nature, such as the beach, birds, rain, or summer night, that facilitate sleep and/or meditation.

In an embodiment, the sound may be emitted down the air delivery conduit 16 to be communicated to the patient's head. Also, the sound may also be sent wirelessly to an audio unit mounted in the mask, headgear, or the patient's head.

Also, the flow generator 210 may include a projection unit, like projection unit 24 of FIGS. 1-2, that may be coordinated with the audio unit 50. For example, the audio unit 50 may generate the audio that accompanies the television program and/or movie displayed by the projection unit. Alternatively, the audio unit 50 may generate ambient sounds that coordinate with the images, e.g., light show, displayed by the projection unit.

Further, the audio unit 50 may be arranged to play compact discs, tapes, and/or electronic music files, e.g., MP3 files.

The aromatic unit 60 is operable to selectively release one or more aromas, e.g., in the form of aromatherapy, through one or more openings provided in walls of the housing 12. In an embodiment, the aromas may be selected to facilitate sleep and/or meditation.

In another embodiment, the aromatic unit may administer inhalation therapies, inhalation medications, and/or drugs into the air delivery conduit 16 communicated with the patient interface. The inhalation therapies, inhalation medications, and/or drugs may include atomized, aerosol, and/or particulate drugs, and may be delivered into the air delivery path anywhere between the flow generator and the patient interface. The aromatic unit may be integrated with the flow generator or may be a separate unit with a bypass tube to add the drug into the air delivery path.

Further, the aromatic and/or medication level may adjust according to a level of nasal congestion, e.g., higher airway impedance.

Also, the aromatic unit 60 may be coordinated with the projection unit and/or the audio unit 50. For example, the aromatic unit 60 may selectively release aromas that accompany the image displayed by the projection unit and/or the audio generated by the audio unit 50. In an embodiment, the aromatic unit 60 may selectively release aromas of the beach, and the audio unit 50 may generate sounds of the beach.

Control of Projection, Audio, and/or Aromatic Unit

Figure 4:
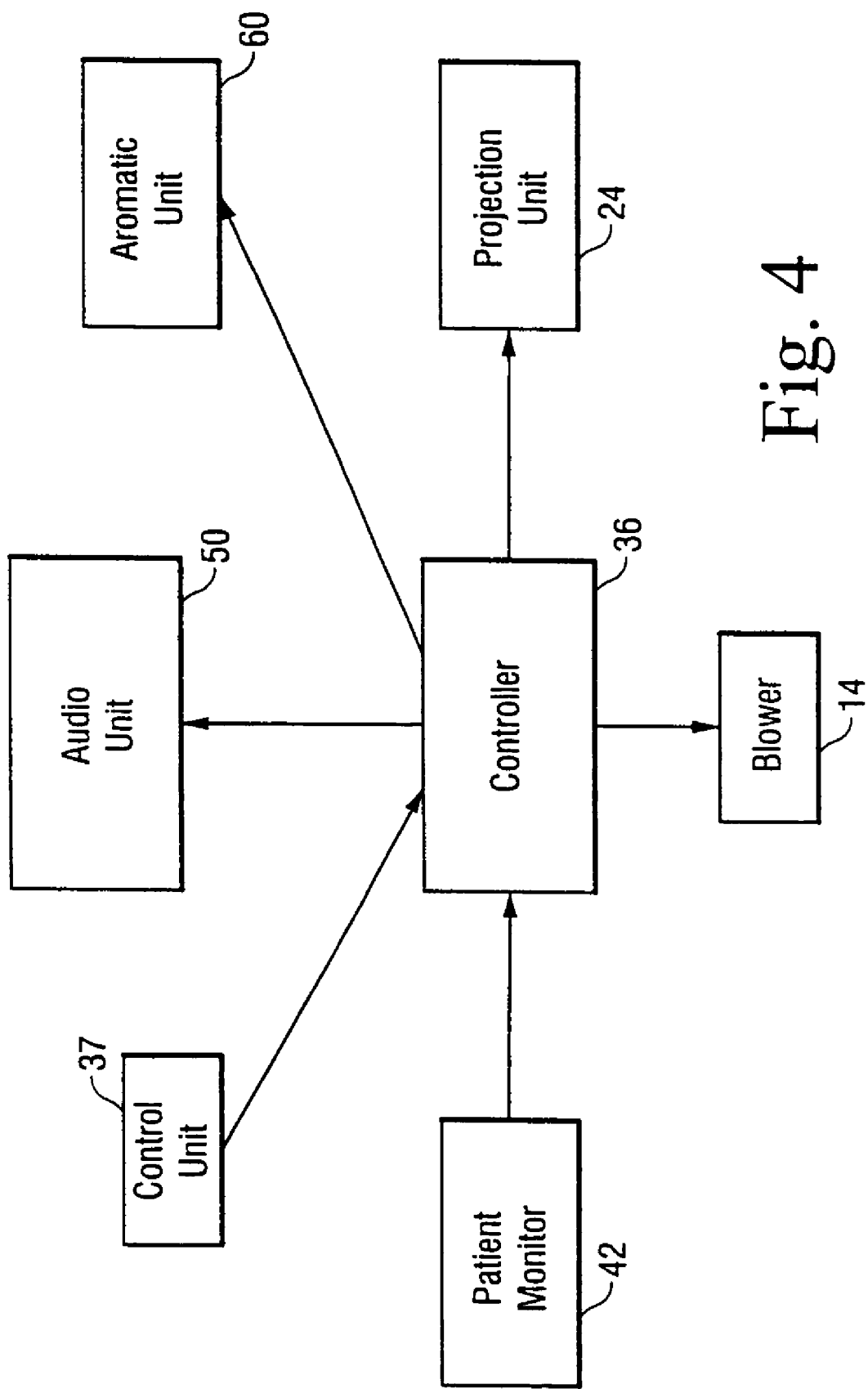
FIG. 4 is a schematic view of a controller that controls operation of a flow generator in accordance with an embodiment of the present invention.

As best shown in FIG. 4, the flow generator 10, 210 of either FIG. 1, 2, or 3 may include a controller 36 operable to receive input signals and to control operation of the blower 14, the projection unit 24, the audio unit 50, and/or the aromatic unit 60 based on the input signals. The input signals may be provided by a control unit 37 having a plurality of control features that can be manually selected and/or adjusted by the patient. For example, the patient may adjust the blower outlet pressure and/or the desired image to be projected by the projection unit 24.

Figure 5:
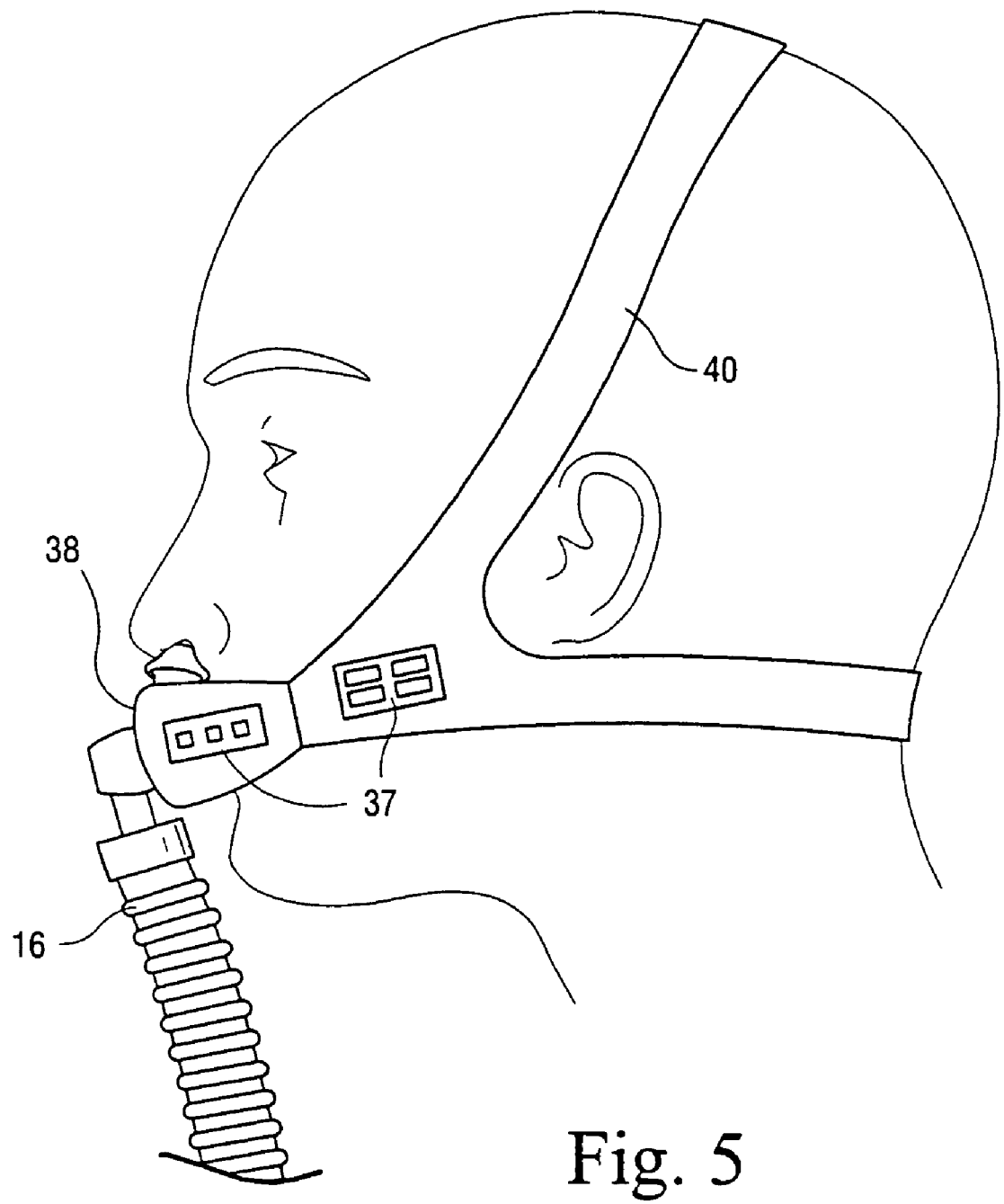
FIG. 5 is a side view illustrating a mask assembly according to another embodiment of the present invention, wherein control features are incorporated into the patient interface and/or headgear arrangement.

In an embodiment, the control unit 37 may be provided on the housing 12. In another embodiment, the control unit 37 may be a remote-type control unit that communicates with the controller 36, e.g., wirelessly. In yet another embodiment, the control unit 37 may be incorporated into a patient interface 38 and/or headgear arrangement 40 as shown in FIG. 5.

Also, the flow generator 10 may include a patient monitor 42 operable to monitor at least one patient parameter and generate at least one input signal to the controller 36. In an embodiment, the patient monitor 42 may be integrated into the patient interface and monitor the respiratory airflow or effort of the patient which may be associated with the patient's sleep state. In another embodiment, the patient monitor 42 may include a heart-rate monitor or any other relevant parameter, including combinations of parameters. Based on information received from the patient monitor 42, the controller 36 may selectively control operation of the blower 14, the projection unit 24, the audio unit 50, and/or the aromatic unit 60.

For example, the controller 36 may adjust the image 26 of the projection unit 24 based on the monitored parameter, e.g., sleep state. In one embodiment, the projection unit 24 may be controlled (based on the sensed parameter) to display an image 26 as the patient is falling asleep, and then gradually fade out the image 26 as the patient falls deeper into sleep. In another embodiment, the projection unit 24 may be controlled to adjust the substance of the image 26 based on the monitored parameter. The parameter that is used to control the projection unit may be a parameter that is already monitored in existing flow generators or mask systems. Moreover, the controller 36 may adjust parameters of the blower 14, e.g., blower outlet pressure, based on the monitored parameter.

Similar to the projection unit 24, the audio unit 50 may be selectively controlled based on information received from a manual control unit 37 and/or a patient monitor 42 monitoring one or more patient parameters as shown in FIG. 4. In one embodiment, the controller 36 may adjust the volume of the audio unit 50 based on the monitored parameter. For example, the monitored parameter may be the volume of the patient's breathing. Thus, the controller 36 may decrease the volume of the audio unit 50 when the patient's breathing is relatively soft for a sustained amount of time (e.g., 5-10 minutes), and/or the controller 36 may increase the volume of the audio unit 50 (e.g., canceling noise) when the patient's breathing is relatively loud for a sustained amount of time (e.g., 5-10 minutes). In this arrangement, the audio unit 50 functions as a noise canceling device to muffle the patient's breathing so it does not wake the patient and/or bed partner during sleep.

In another embodiment, the controller 36 may continuously vary the volume of the audio unit 50 based on the patient's sleep state. For example, the volume may be higher at the beginning of sleep, and the volume may be gradually decreased as the patient falls deeper in sleep.

As shown in FIG. 4, the aromatic unit 60 may also be selectively controlled based on information received from a manual control unit 37 and/or a patient monitor 42 monitoring one or more patient parameters. In one embodiment, the controller 36 may continuously vary the quantity of aroma being released based on the patient's sleep state. For example, the quantity may be higher at the beginning of sleep, and the quantity may be gradually decreased as the patient falls deeper in sleep.

Also, any one of the projection unit 24, audio unit 50, and aromatic unit 60 may simply be timed with a clock. That is, operation of the projection unit 24, audio unit 50, and/or aromatic unit 60 may be determined by a clock setting, e.g., on/off time, elapsed time, etc.

Patient Interface and/or Headgear with Control Unit

As noted above and illustrated in FIG. 5, a control unit 37 with one or more control features of the flow generator 10, 210 may be incorporated into the patient interface 38 and/or headgear arrangement 40. This configuration allows the patient to easily adjust one or more parameters of the flow generator 10, 210 without being adjacent to the flow generator 10, 210. The control features may be wirelessly communicated with the projection unit 24, audio unit 50, and/or aromatic unit 60 to avoid cables that may irritate or become tangled with the patient.

Headgear with Audio Unit

In an alternative embodiment, the entire assembly (including the controls and the projection unit 24, audio unit 50, and/or aromatic unit 60) may be provided in the patient interface 38 and/or headgear arrangement 40.

Figure 6:
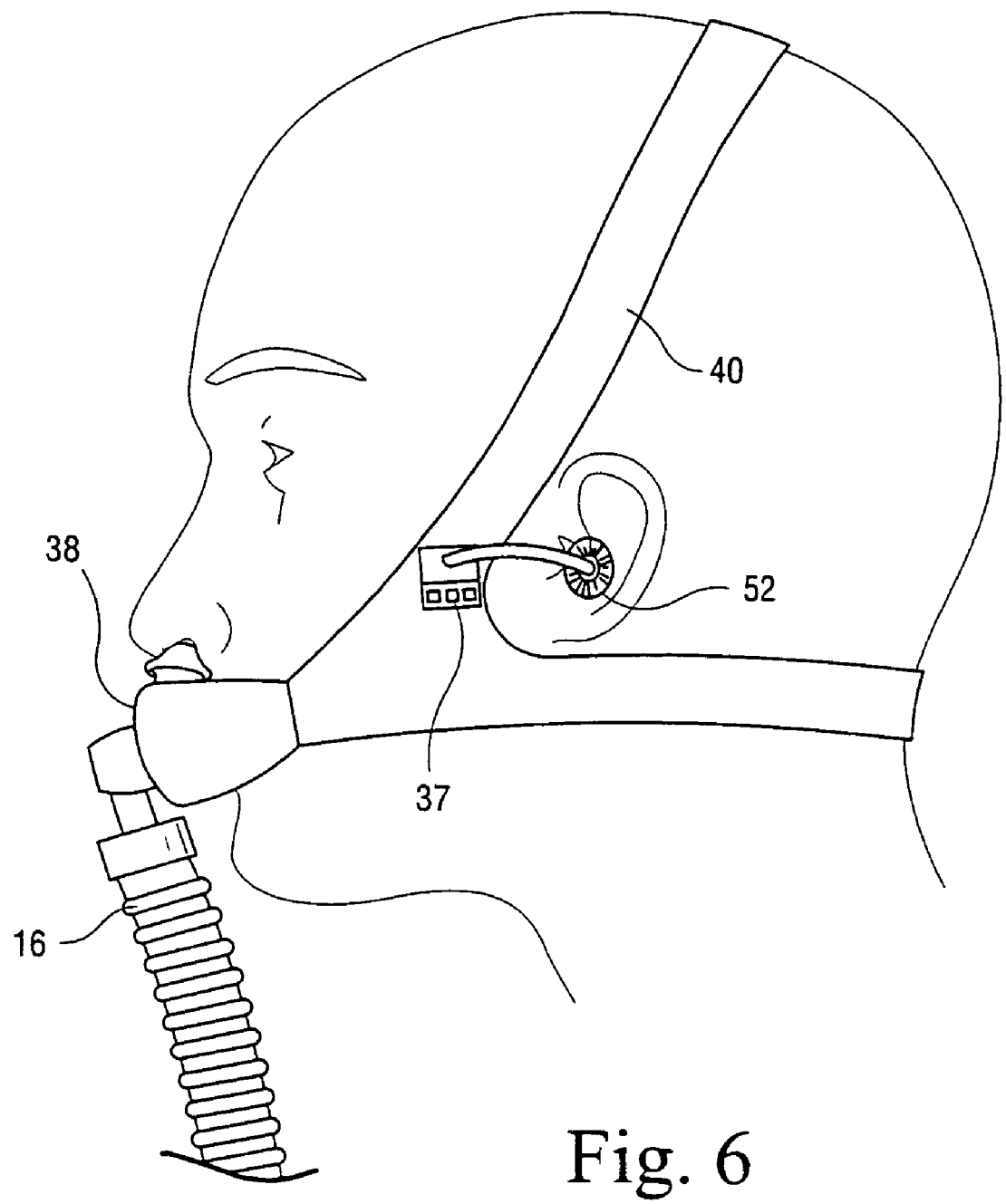
FIG. 6 is a side view illustrating a mask assembly including an audio unit according to another embodiment of the present invention, wherein earphones are incorporated into a headgear arrangement.

FIG. 6 illustrates an embodiment wherein the audio unit 50 may be incorporated into the patient interface or headgear arrangement rather than the flow generator 210. As illustrated, straps of the headgear arrangement 40 adjacent the patient's ears may support speakers and/or earphones 52. This arrangement allows the audio, e.g., music, to be delivered directly to the patient without disturbing the patient's bed partner. Also, a control unit 37 (buttons, dial-type volume/frequency control, etc.) may be incorporated into the headgear arrangement 40 to control parameters of the audio unit 50. While FIG. 6 shows an arrangement where the audio unit is built into the headgear straps, the audio unit may be formed as a stand-alone unit that can be retrofitted onto headgear, e.g., via a clip or Velcro®, etc. The audio unit can be used to transmit sounds that are coordinated with transmissions from a projection unit.

Headgear with Aromatic Unit

Figure 7A:
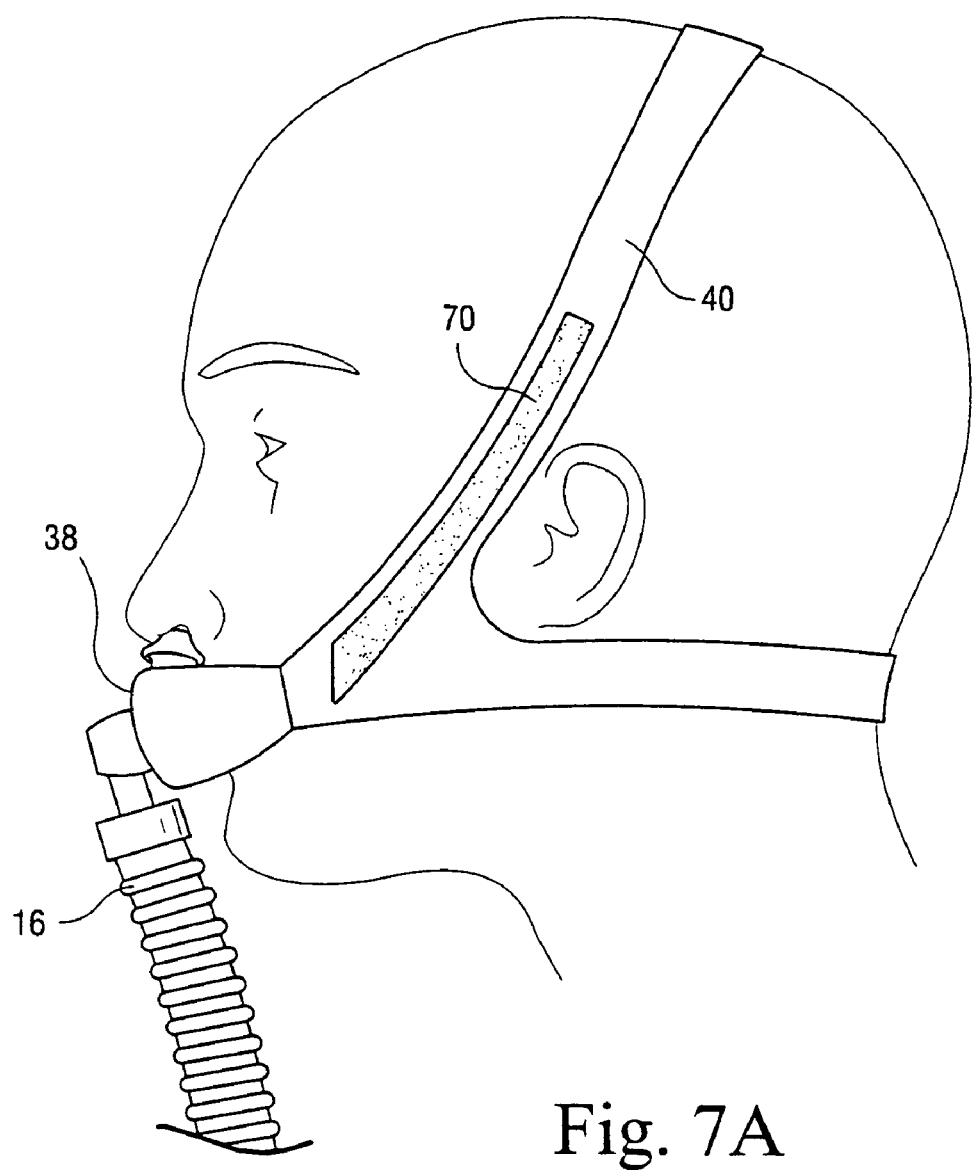
FIGS. 7A-7B illustrate a mask assembly according to still another embodiment of the present invention, wherein an aromatic unit is incorporated into the headgear arrangement.
Figure 7B:
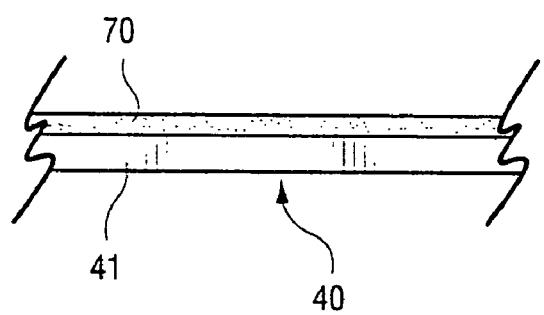

As shown in FIG. 7A, the aromatic unit 60 may be in the form of aromatic strips 70 that are incorporated into the headgear arrangement 40. Specifically, aromatic strips 70 may be attached, e.g., by stitching, to one or more straps 41 of the headgear arrangement 40 as best shown in FIG. 7B. The aromatic strips 70 may be heat-activated or activated in any other suitable manner. For example, the strips 70 may be passively activated and deactivated by the patient's body heat depending on whether the headgear is being worn or not. Alternatively, the controller may activate and deactivate the strips, e.g., via electrical stimulation, based on one or more sensed parameters of the patient and/or blower, or by coordinating with an alarm clock, etc.

Alarm

In an embodiment, an alarm may be incorporated into the flow generator 10, 210, patient interface 38, and/or headgear arrangement 40. For example, the alarm may be incorporated into the audio unit 50.

Also, a sleep stage monitor may monitor a patient's sleep stage and then activate the alarm based on the patient's sleep stage. It is known in the art that waking a person during a certain sleep stage, e.g., shallow sleep stage, or a particular part of the REM-NREM sleep cycle will make one feel more alert and energetic.

Thus, the sleep stage monitor may monitor the patient's sleeping pattern throughout the night and activate the alarm to wake-up the patient when it is the best time to wake-up the patient based on sleep stages, sleep cycles, and the quality of the sleep. The sleep stage monitor and alarm may be referred to as a sleep clock.

Also, the sleep clock may be used as a training tool until a regular sleeping pattern is established by the patient if the patient has a sleeping disorder related to sleeping patterns. However, the sleep clock may be used by anyone who would like to improve his/her quality of sleep.

It is noted that the sleep stage monitor may be incorporated into a flow generator, patient interface, and/or headgear arrangement.

In another embodiment, a basic alarm clock, i.e., a clock that may be set to provide an audio/visual alarm (e.g., a light, buzzer, or bell) at a desired time, may be incorporated into the flow generator. No additional hardware may be required to incorporate the basic alarm clock, e.g., an algorithm may be introduced into the flow generator software to provide the basic alarm clock features. This allows the existing control unit (e.g., real time clock, speaker, LCD, and keypad) provided to the flow generator to be used for programming and operating the alarm clock. If the flow generator is relatively portable, the basic alarm clock feature may be particularly useful for patient's who travel with the portable flow generator. In alternative embodiments, a basic alarm clock may be incorporated into the patient interface, and/or headgear arrangement.

Sleep Stage Monitor Coordinated with Drug/Hormone Treatment

In another embodiment, a sleep stage monitor may be coordinated with drug and/or hormone treatment. That is, the release of drug and/or hormone treatment may be based on the patient's sleep stage as treatment may be more optimal at certain sleep stages.

For example, it is known that certain growth hormones are released at certain parts of the sleep cycles, and that hormones are one of key factors that control our well-being, the recovery of the body's aging process, and the rest of mind. Thus, coordinating the release of hormone treatment with the patient's sleep stage via a sleep stage monitor would be more natural. Moreover, the release of hormone treatment may be performed in a controlled manner, at a regulated pattern, and at particular parts of the sleep cycle.

The sleep stage monitor may be incorporated into a flow generator, patient interface, and/or headgear arrangement. Also, the drug and/or hormone treatment may be delivered into the air delivery path anywhere between the flow generator and the patient interface. Moreover, the drug and/or hormone treatment may include atomized, aerosol, and/or particulate drugs, and the treatment may be provided in a module that is incorporated into a flow generator, patient interface, and/or headgear arrangement.

It is noted that the sleep stage monitor may also be coordinated with the projection unit 24, the audio unit 50, and/or the aromatic unit 60 so that the visual, audio, and/or aromatic medium may be provided based on the patient's sleep stage.

Embodiment of Sleep Stage Monitor

Figure 8:
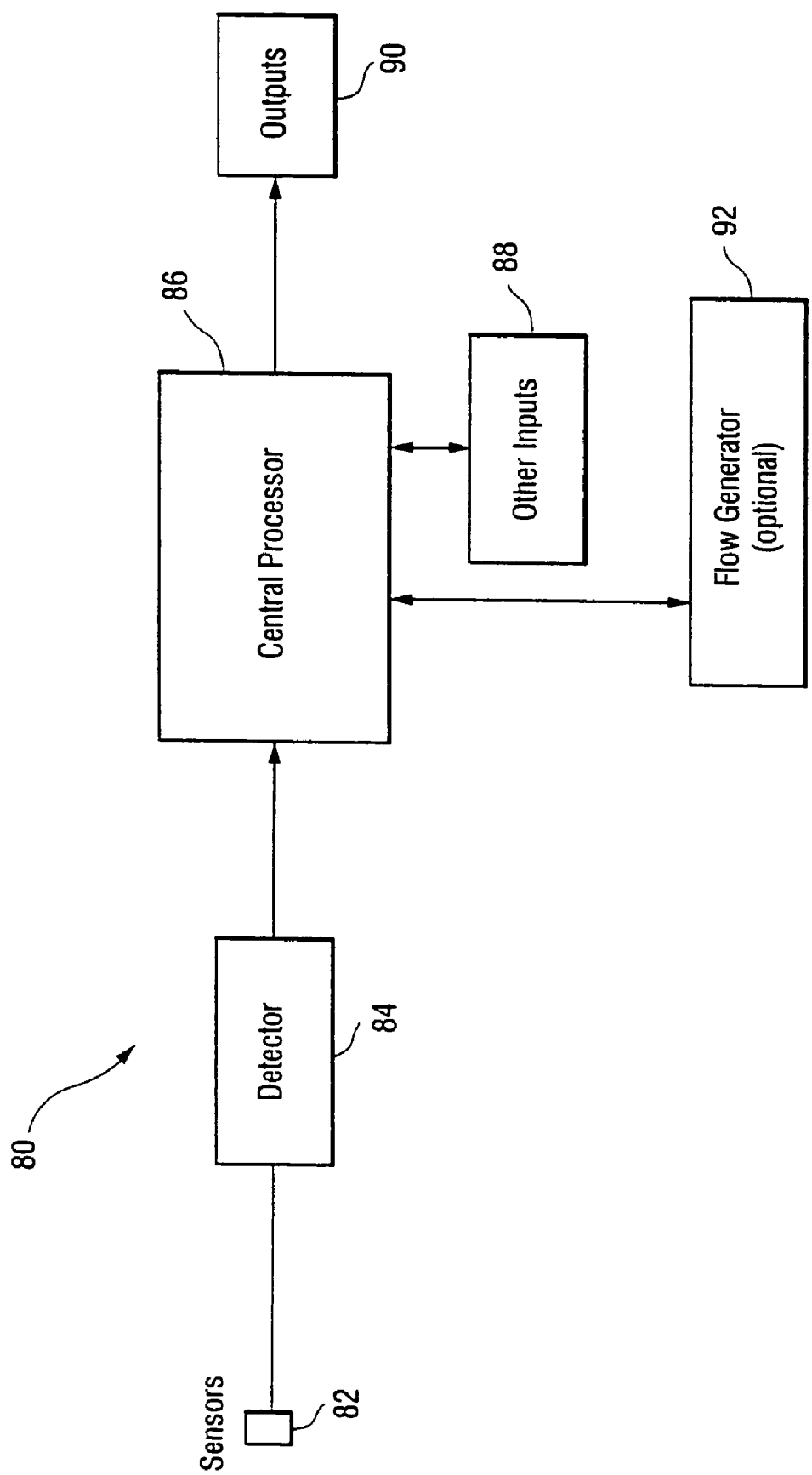
FIG. 8 is a schematic view of a sleep stage monitor according to an embodiment of the present invention.

FIG. 8 is a schematic view that illustrates an embodiment of a sleep stage monitor structured to monitor a person's sleeping pattern and clearly identify the NREM and REM sleep cycles and the durations of each cycle.

As illustrated, the sleep stage monitor 80 includes sensors 82 that sense or monitor aspects of a person's body. Monitoring may be done by detecting eye movement or by receiving signals from electrodes attached to parts of a person's body. Eye movement may be detected by eye sensors that may be worn on the person's forehead like spectacles or headbands. Also, the eye sensors may be incorporated into the patient interface and/or headgear arrangement. The electrodes, e.g., body or face electrodes, may be in the form of a patch with small suction pads so it attaches to the person's skin.

Signals from the sensors 82 are detected, enhanced, and amplified by the detector 84 before they are communicated to the central processor 86. The central processor 86 analyzes the signals and determines the part of the sleep cycle the person is at, the quality of the sleep, and/or the number of sleep cycles completed. Also, the central processor may gather and analyze information from other inputs 88, such as the blood $O_2$ and the $CO_2$ levels. As illustrated, the central processor 86 may be a separate module or may be incorporated into a flow generator 92, for example.

The clinician can decide which sleep pattern is best suited for each person, e.g., based on the patient's age and other physical conditions, and the patient can input how many hours of sleep he/she would like to have each night based on his/her workload or tiredness during the day. Thus, the outputs 90 are driven according to the sleep pattern selected by the clinician, the inputs selected by the user, and the quality of the sleep monitored from the sensors. The selected sleep pattern may be controlled by a software program that is based on stored medical data in the monitor 80 or in a computer. Thus, the information may be updated to enhance the programs.

The central processor 86 may have a large memory to record the sleeping patterns and other information. The recorded information may be used by a clinician to study the patients sleeping pattern and to enhance the treatment. Also, the monitor 80 may be connected to a network and be monitored remotely.

As explained above, the output 90 may be used to trigger an alarm, visual, audio, and/or aromatic medium that stimulates human senses. Also, the output 90 may trigger the release of medication or hormone treatment. Additionally, the monitor 80 may be programmed to wake-up or reset a person's sleep if he/she is having a very restless sleep due to physical reasons, bad dreams, and/or REM behavior disorders that arise during the night.

The combination of the monitor 80 and a flow generator would not only treat sleep apnea but would also enhance the quality sleep.

Additional Embodiments

Figure 9:
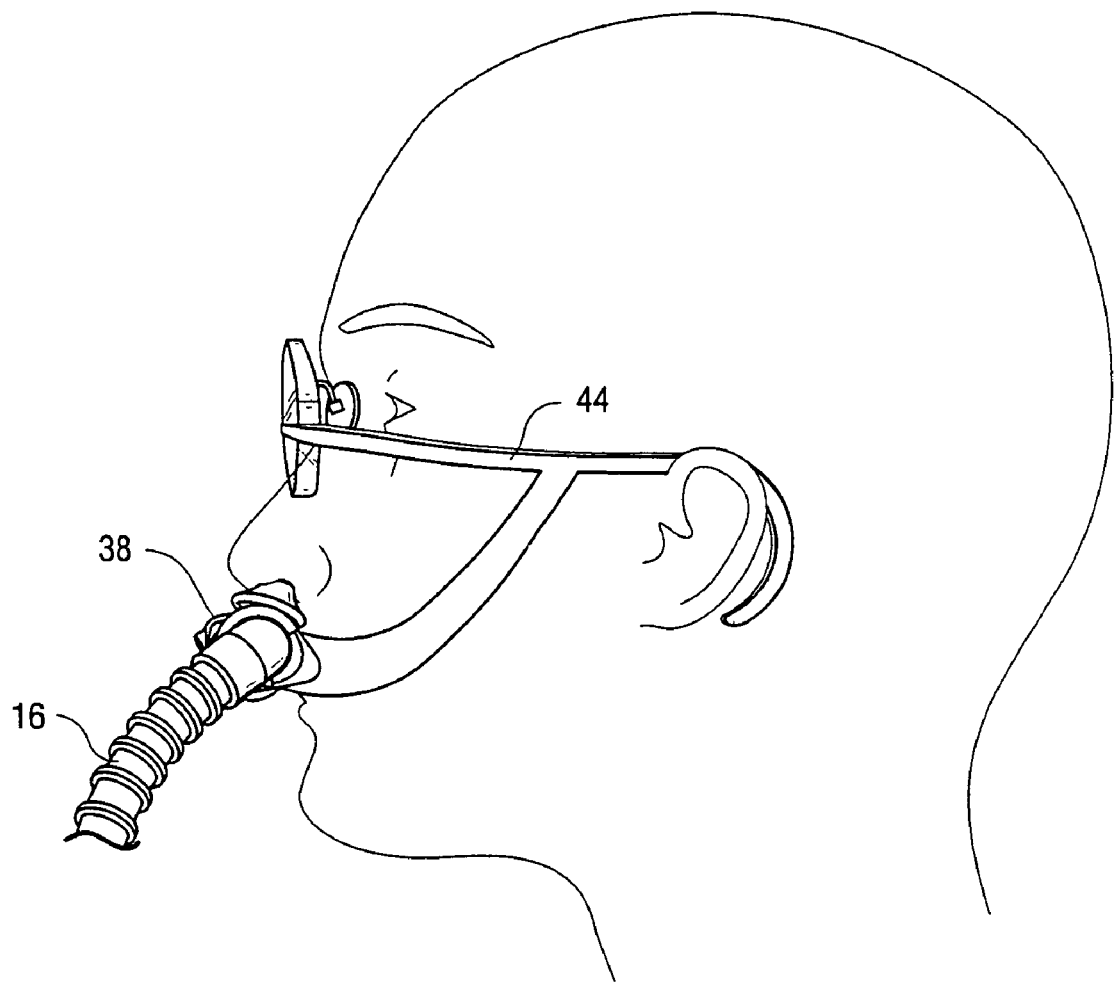
FIG. 9 is a side view illustrating a patient interface integrated with eyeglasses according to yet another embodiment of the present invention.

In another embodiment, as shown in FIG. 9, the patient interface 38, e.g., nasal prongs, may be integrated with the patient's eyeglasses 44. This arrangement may provide more comfort to the patient. Furthermore, the eyeglass material may be constructed from flexible water clear material such as silicone rubber or polyester to prevent contacted pressure sores if the glasses are dislodged relative to the patient's face.

In still another embodiment, the flow generator may include a camera and/or infrared lighting to allow further monitoring of a patient's condition. The camera and/or infrared lighting may include one or more features, e.g., a shutter, to allow the patient to maintain privacy as desired.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A flow generator for generating a supply of pressurized air to be provided to a patient for treatment, the flow generator comprising:
   a housing;
   a blower provided to the housing, the blower operable to provide a pressurized flow of air at an outlet; and
   a projection unit provided to the housing, the projection unit being operable to project an image onto a surface adjacent the housing.

2. The flow generator according to claim 1, wherein the projection unit is controlled based on at least one monitored parameter of the patient.

3. The flow generator according to claim 1, further comprising a controller operable to control operation of the blower and the projection unit.

4. The flow generator according to claim 3, further comprising a patient monitor operable to monitor at least one patient parameter and generate at least one input signal to the controller.

5. The flow generator according to claim 4, wherein the at least one parameter includes patient respiratory airflow or breathing effort.

6. The flow generator according to claim 4, wherein the projection unit is controlled in accordance with the input signal.

7. The flow generator according to claim 1, further comprising an audio unit provided to the housing, the audio unit operable to selectively generate at least one sound.

8. The flow generator according to claim 7, wherein the at least one sound is at least one of music, soothing sounds, white noise, and noise canceling.

9. The flow generator according to claim 7, wherein the audio unit is controlled based on at least one monitored parameter of the patient.

10. The flow generator according to claim 1, further comprising an aromatic unit provided to the housing, the aromatic unit operable to selectively release at least one therapeutic aroma.

11. The flow generator according to claim 10, wherein the aromatic unit is controlled based on at least one monitored parameter of the patient.

12. The flow generator according to claim 1, wherein the housing includes an upper wall, a lower wall, and side walls that interconnect the upper and lower walls.

13. The flow generator according to claim 12, wherein the image is projected from the housing through an opening provided in the upper wall.

14. The flow generator according to claim 12, wherein the image is projected from the housing through an opening provided in one of the side walls.

15. The flow generator according to claim 1, wherein the image includes a light show.

16. The flow generator according to claim 15, wherein the light show includes continuously changing colors or images.

17. The flow generator according to claim 1, wherein the image includes a control panel having a virtual keyboard.

18. The flow generator according to claim 1, wherein the housing is supported on a bedside table, and the surface is a surface of the bedside table.

19. The flow generator according to claim 1, wherein the surface is a wall.

* * * * *